United States Patent [19]

Palva

[11] Patent Number: 5,010,000

[45] Date of Patent: Apr. 23, 1991

[54] METHOD FOR THE PREPARATION OF A SELECTED PROTEIN OR A PART THEREOF IN BACILLUS STRAIN BACTERIA

[75] Inventor: Ilkka Palva, Helsinki, Finland

[73] Assignees: Genesit Oy; Oy Alko AB, both of Helsinki, Finland

[21] Appl. No.: 129,356

[22] Filed: Nov. 30, 1987

Related U.S. Application Data

[63] Continuation of Ser. No. 520,036, Aug. 3, 1983, abandoned, which is a continuation-in-part of Ser. No. 336,405, Dec. 31, 1981, abandoned.

[30] Foreign Application Priority Data

Dec. 31, 1980 [FI] Finland .................................. 804081

[51] Int. Cl.$^5$ .................... C12P 21/00; C12N 15/00; C12N 1/20; C12N 9/86
[52] U.S. Cl. .................................. 435/69.1; 435/69.51; 435/69.7; 435/69.8; 435/77.2; 435/172.3; 435/252.31; 435/320.1; 435/231; 935/48; 935/74
[58] Field of Search .................. 435/68, 70, 71, 91, 435/172.1, 172.3, 183, 202, 243, 253, 320, 252.3, 252.31–252.35, 69.1, 69.51, 69.7, 69.8, 71.2, 231; 536/27; 935/9–15, 29, 33, 38, 47, 48, 74

[56] References Cited

U.S. PATENT DOCUMENTS

4,338,397  7/1982  Gilbert et al. ........................ 435/70

FOREIGN PATENT DOCUMENTS

| 0003062 | 7/1979 | European Pat. Off. |         |
|---------|--------|--------------------|---------|
| 0006694 | 1/1980 | European Pat. Off. | 435/172.3 |
| 0034470 | 8/1981 | European Pat. Off. | 435/172.3 |
| 0036259 | 9/1981 | European Pat. Off. | 435/172.3 |
| 0021468 | 4/1983 | European Pat. Off. | 435/172.3 |
| 1521032 | 8/1978 | United Kingdom     | 435/172.3 |
| 2031905 | 4/1980 | United Kingdom     | 435/172.3 |
| 1588572 | 4/1981 | United Kingdom     | 435/172.3 |
| 2071671 | 9/1981 | United Kingdom     | 435/172.3 |

OTHER PUBLICATIONS

Yoneda et al: Biochem. Biophys. Res. Comm. 91: 1556 (1979).
Takkinen et al: J. Biol. Chem. 258: 1007 (1983).
Ohmura et al: Biochem. Biophys. Res. Comm. 112: 678 (1983).
Yang et al: Nucleic Acids Res. 11: 237 (1983).
Gryczan et al: Molec. Gen. Genet. 177: 459 (1980).
Keggins et al: Proc. Natl. Acad. Sci. U.S.A. 75: 1423 (1978).
Lovett and Keggins, Meth. Enzymol. 68: 342–357 (1979).
Priest, Bacteriol. Rev. 41(3): 711–753 (1977).
Palva et al., Gene 15: 43–51 (1981).
Palva, Gene 19: 81–87 (1982).
Palva et al., Proc. Natl. Acad. Sci. U.S.A. 79: 5582–5586 (1982).
Palva et al., Gene 22: 229–235 (1983).

Primary Examiner—James Martinell
Attorney, Agent, or Firm—Sterne, Kessler, Goldstein & Fox

[57] ABSTRACT

A selected protein or protein part is prepared in Bacillus strain bacteria by joining DNA encoding the selected protein or protein part essential to its biological activity to a bacterium gene. The *Bacillus amyloliquefaciens* gene for α-amylase is cleaved at a location after the excretion signal following the regulation sequence, or at a location after a part essential with respect to its excretion. The cleaved gene is joined to a plasmid present in Bacillus strain bacteria in several copies, and the DNA sequence encoding the selected protein or protein part essential to its biological activity is joined to the cleavage site by recombinant DNA techniques. Bacillus strain host bacteria are transformed with the recombinant DNA molecules so obtained, and the transformed host bacteria cultivated to produce the selected protein or protein part.

8 Claims, 5 Drawing Sheets

```
        Cla I
      Taq I
5'  GGA TCG A T GTT TGA GAA AAG AAG ACC
3'  CCT AGC TAA CAA ACT CTT TTC TTC TGG
             10          20

ATA AAA ATA CCT TGT CTG TCA TCA GAC AGG GTA TTT TTT ATG
TAT TTT TAT GGA ACA GAC AGT AGT CTG TCC CAT AAA AAA TAC
            40          50          60

CTG TCC AGA CTG TCC GCT GTG TAA AAA ATA GGA ATA AAG GGG
GAC AGG TCT GAC AGG CGA CAC ATT TTT TAT CCT TAT TTC CCC
 70          80          90          100

GGG TTG TTA TTA TTT TAC TGA TAT GTA AAA TAT AAT TTG TAT
CCC AAC AAT AAT AAA ATG ACT ATA CAT TTA ATA TTA AAC ATA
110         120         130         140         150

Met Phe Gln Lys Arg Lys Arg
                                  Hinf I
AAG AAA ATG AGA GGG AGA GGA AAC ATG ATT CAA AAA CGA AAG CGG
TTC TTT TAC TCT CCC TCT CCT TTG TAC TAA GTT TTT GCT TTC GCC
            160         170                     190
                              180

Thr Val Ser Phe Arg Leu Val Leu Met Cys Thr Leu Leu Phe Val

ACA GTT TCG TTC AGA CTT GTG CTT ATG TGC ACG CTG TTA TTT GTC
TGT CAA AGC AAG TCT GAA CAC GAA TAC ACG TGC GAC AAT AAA CAG
   200         210         200         230         240

Ser Trp Pro Ile Thr Lys Thr Ser Ala Val Asn Gly Thr Leu Met

AGT TTG CCG ATT ACA AAA ACA TCA GCC GTA AAT GGC ACG CTG ATG
TCA AAC GGC TAA TGT TTT TGT AGT CGG CAT TTA CCG TGC GAC TAC
            250         260         270         280

Gln Tyr Phe Glu Trp Tyr Thr Pro Asn Asp Gly Gln His Trp Lys
                                    Hae III
CAG TAT TTT GAA TGG TAT ACG CCG AAC GAC GGC CAG CAT TGG AAA
GTC ATA AAA CTT ACC ATA TGC GGC TTG CTG CCG GTC GTA ACC TTT
   290         300         310         320         330
```

*FIG. 3A*

```
Arg Leu Gln Asn Asp Ala Glu His Leu Ser Asp Ile Gly Ile Thr
                                                    Hinf I
CGA TTG CAG AAT GAT GCG GAA CAT TTA TCG GAT ATC GGA ATC ACT
GCT AAC GTC TTA CTA CGC CTT GTA AAT AGC CTA TAG CCT TAG TGA
        340         350         360         370

Ala Val Trp Ile Pro Pro Ala Tyr Lys Gly Leu Ser Gln Ser Asp

GCC GTC TGG ATT CCT CCC GCA TAC AAA GGA TTG AGC CAA TCC GAT
CGG CAG ACC TAA GGA GGG CGT ATG TTT CCT AAC TCG GTT AGG CTA
        380         390         400         410         420

Asn Gly Tyr Gly Pro Tyr Asp Leu Tyr Asp Leu Gly Glu Phe
                                                    EcoRI
AAC GGA TAC GGA CCT TAT GAT TTG TAT GAT TTA GGA GAA TTC 3'
TTG GCT ATG CCT GGA ATA CTA AAC ATA CTA AAT CCT CTT AAG 5'
        430         440         450         460
```

FIG. 3B 1   2   3

METHOD FOR THE PREPARATION OF A SELECTED PROTEIN OR A PART THEREOF IN BACILLUS STRAIN BACTERIA

This application is a continuation of application Ser. No. 520,036, filed Aug. 3, 1983, and abandoned, which is a continuation-in-part of application Ser. No. 336,405, filed Dec. 31, 1981, and abandoned.

This invention is concerned with a method for the preparation of a selected protein or a part thereof in *Bacillus* strain bacteria by joining DNA coding for the selected protein or a part thereof essential to its biological activity to a bacterium gene. The method comprises cleaving the *Bacillus amyloliquefaciens* gene for α-amylase at a location after the excretion signal following the regulating part or at a location after a part essential with respect to its excretion, joining the cleaved gene to a plasmid present in *Bacillus* strain bacteria in several copies, joining the DNA sequence coding for the selected protein or for a part thereof essential to its biological activity to the cleavage site by recombinant DNA techniques, transforming the *Bacillus* strain host bacteria with the recombinant DNA molecule so obtained and cultivating the transformed host bacteria for producting the selected protein or a part thereof.

As will appear from the following description, the new method can be used to produce any protein in *Bacillus* strain bacteria.

Recent development in molecular biology has created new possibilities for protein production in bacteria by recombinant DNA techniques. By means of recombinant DNA techniques it is possible to produce proteins of prokaryotic and eukaryotic cells in bacteria by joining a gene of the desired protein to a regulating unit of the gene of the host bacterium, whereby any foreign gene can be expressed. In addition, the number of the copies of the desired gene in the cell can be increased by joining the gene to such a plasmid or virus molecule which is found in the cell in several, usually 10 to 100 copies. The increased number of copies of a certain gene in a cell usually also leads to a corresponding increase in the protein synthesis expressed by the gene.

Several experiments of this type have already been carried out by using *E. coli* as host bacterium. However, the use of *E. coli* as cloning host in industrial protein production suffers from the following disadvantages:

(i) *E. coli* is a human intestinal bacterium and, accordingly, in mass production, involves a potential health hazard (ii) when using *E. coli*, the products remain within the cell for which reason the cells must first be collected and broken whereafter the desired product must be purified of the remaining cell components of which some are toxic (endotoxin of *E. coli*)

(iii) when producing proteins within the cell, a foreign protein may be cleaved under the action of intracellular proteases or a foreign protein may inhibit the growth of the cell whereby, in each case, the yield of the desired protein is reduced.

A significant improvement in industrial production would be provided if the host bacterium would be capable of excreting the desired gene product directly into the culture medium outside the cell and if, instead of *E. coli*, a non-pathogenic bacterium could be used. It has been established that excretion of a protein is due to the so-called signal sequence (Blobel, G. and Dobberstein, B., J. of Cell Biology 67: 835–862; 1975) which precedes the first part of the gene coding for the excreting protein and which is similar in prokaryotic and eukaryotic cells (Wakesman et al., Biochimica et Biophysica Acta 604: 249–296, 1980). Recombinant DNA techniques has made it possible to isolate the DNA coding for the signal sequence of any excreting protein and to join it to the desired gene.

In the U.S. patent application Ser. No. 913,533 (Harvard), this general principle has been applied by joining a foreign gene (e.g. the gene coding for insulin) to the cleavage site of the restriction enzyme located in the centre of the TEM β-lactamase of *E. coli*, whereby the obtained fusion protein can be made to excrete into the so-called periplasmic space between two cell membranes of *E. coli*. Although the product, in this way, could be protected against intracellular proteases, the basic problems associated with the use of *E. coli* remain also in this method: a potential health hazard in mass production and difficult isolation and purification processes because the product, also in this case, still remains within *E. coli* cell. Corresponding excreting hybrid proteins have also been produced in *E. coli* by gene fusion techniques.

The use of *Bacillus* strain bacteria as cloning host is only beginning due to the relatively limited amount of knowledge and techniques of the bacteria of this strain as compared to *E. coli* (Gryczan, T. et al., Molecular General Genet. 117: 459–467, 1979; Keggins, K. M. et al., Proc. Natl. Acad. Sci. U.S.A. 75: 1423–1427, 1978; Yoneda, Y. et al., Biochem. Biophys. Res. Commun. 91: 1556–1564, 1979). Because the *Bacillus* strain bacteria nevertheless excrete several different proteins, for example, proteases, α-amylase, ribonuclease, and penicillinase directly into their culture medium (Priest, F. Bacteriol. Rev. 41: 711–753, 1977) and a plurality of said bacteria are apathogenic, they form a potentially important cloning host group when developing industrial protein production.

In the U.S. patent application Ser. Nos. 128,537 and 221,800 (Cetus) the corresponding general principle has been used by forming a *Bacillus* vector in which a foreign gene has been joined to the promotor and signal sequence of the penP gene from *B. licheniformis*. In addition to the fact that the expression level of the gene is substantially lower than that of the α-amylase gene used by the applicant (Palva, I., Gene, 19: 81–87, 1982) the excretion signal of the product of the penP gene is quite exceptional in structure (Lai et al., Proc. Natl. Acad. Sci. U.S.A. 78: 3506–3510, 1981; Nielsen, J. et al., Proc. Natl. Acad. Sci. U.S.A. 78: 3511–3515, 1981) which may be the reason why a large amount of the synthetized protein remains adhered to the cell wall. The liberation of penicillinase or the product of the foreign gene joined to its signal into the culture medium obviously requires the action of the non-specific exoproteases of the cell which, because of the preservation of the foreign gene product, must necessary be removed (Palva, I., Thesis, 1983). Thus, the significant advantage associated with the use of *Bacillus*, i.e. the direct excretion of the product into the substrate, cannot be achieved when using the penP gene. α-amylase and the products joined to its signal, by contrast, are efficiently excreted directly into the culture medium.

This invention describes methods for the separation of the promotor and signal section of α-amylase and for the construction of a special excretion vector for producing any foreign protein in the culture medium of *Bacillus* strain bacteria. The α-amylase gene of *B.*

*amyloliquefaciens* was selected for the construction of the secretion vector because it contains an efficient promotor and the entire synthetizing enzyme is excreted into the culture medium.

BRIEF DESCRIPTION OF THE DRAWINGS

The invention is further illustrated and explained with reference to the attached drawings in which:

FIG. 3 depicts part of the α-amylase gene base order starting at the cleavage site of the restriction enzyme EcoR I.

The proteins were detected with anti E1-serum and protein A, marked $^{125}$I. Lane 1, represents complete Semliki Forest virus; Lane 2, represents B. subtilis IHO/6140 (pKTH51-E1) cells, and Lane 3, represents B. subtilis IHO (pKTH51-E1) culture supernatant.

Figure 1:
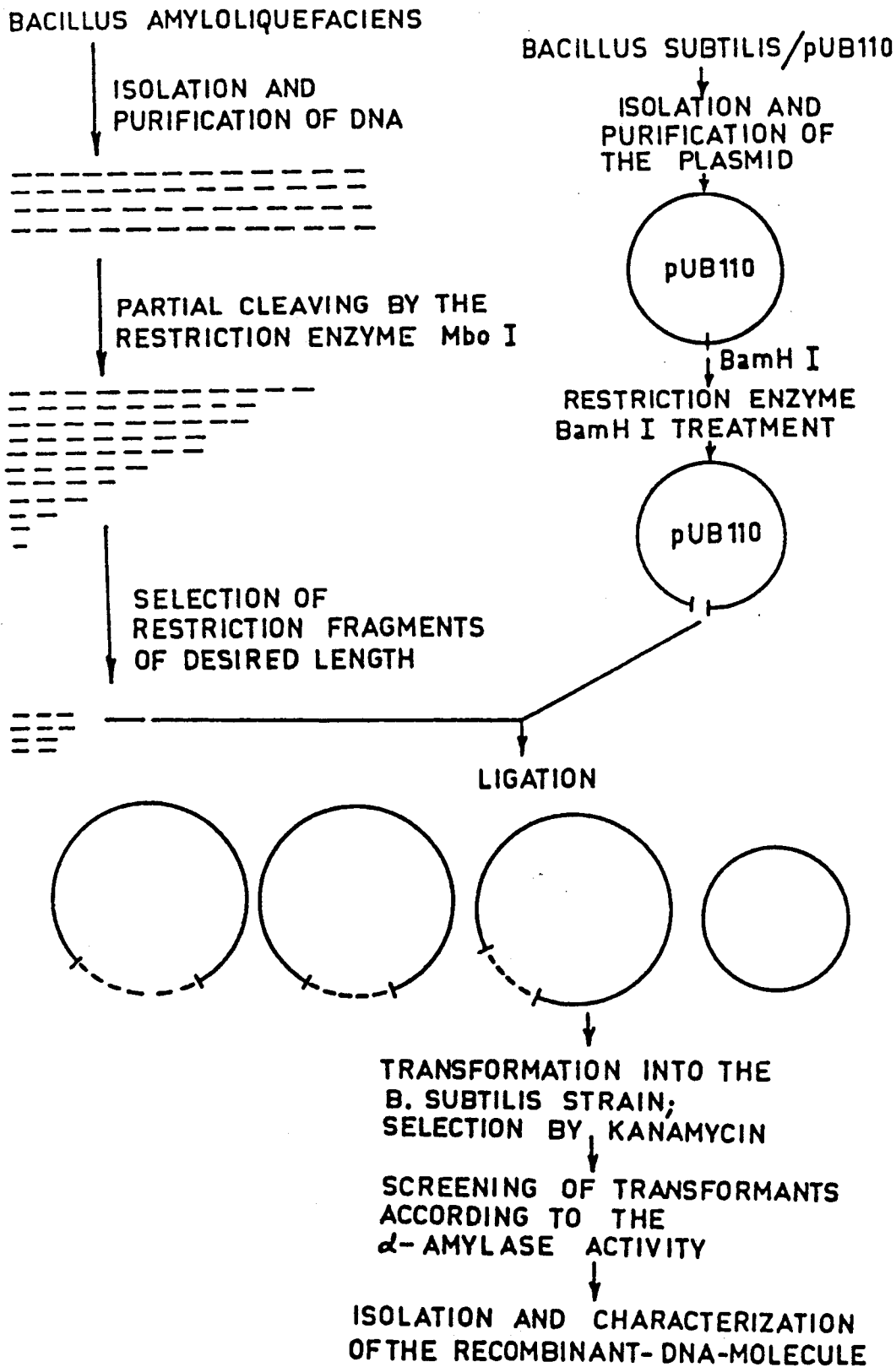
FIG. 1 is a flow chart illustrating diagrammatically the isolation of the gene coding for α-amylase from *Bacillus amyloliquefaciens*.

FIG. 1 is a scheme of the isolation of the gene coding for α-amylase from *Bacillus amyloliquefaciens*. The genome of the whole bacterium is isolated from the *Bacillus* strain bacterium producing α-amylase and cleaved by a restriction enzyme. DNA sequences of a desired length are joined to the plasmid molecule cleaved by the restriction enzyme. According to this invention, the genome of the bacterium can be cleaved by the restriction enzyme Mbo I, and pUB 110 can be used as the plasmid which can be cleaved by the restriction enzyme BamH I. It must be noticed that a corresponding recombinant DNA molecule can be prepared also by using other restriction enzymes or plasmids, and person skilled in the art can choose between various restriction enzyme/plasmid combination without departing from the scope of this invention.

After joining the DNA sequences with the plasmid molecules, the obtained recombinant DNA molecules are transferred into the host bacterium, and from these those bacterium cells are screened that have received a gene coding for α-amylase joined to the plasmid. The screening is based on the achieved ability of the transformed cell to produce α-amylase.

*Bacillus subtilis* strain is used as the host bacterium in the invention. When the above mentioned recombinant DNA molecule has been transferred into the strain, the gene coding for α-amylase is present in the strain in about 50 copies. This increases the α-amylase production of the strain to about 2,500 fold, as compared to the normal *B. subtilis* strain. The 2,500-fold increase of the α-amylase production is due, on the one hand, to the regulation part of the α-amylase gene of the *B. amyloliquefaciens* strain used as the initial strain being more effective than the regulation part of the *B. subtilis* α-amylase gene, and on the other hand, to the number of the α-amylase gene growing 50 fold. In laboratory conditions a *B. subtilis* strain containing a recombinant DNA molecule produces 5 times more α-amylase than *B. amyloliquefaciens* strain used in the isolation of the gene.

Figure 2:
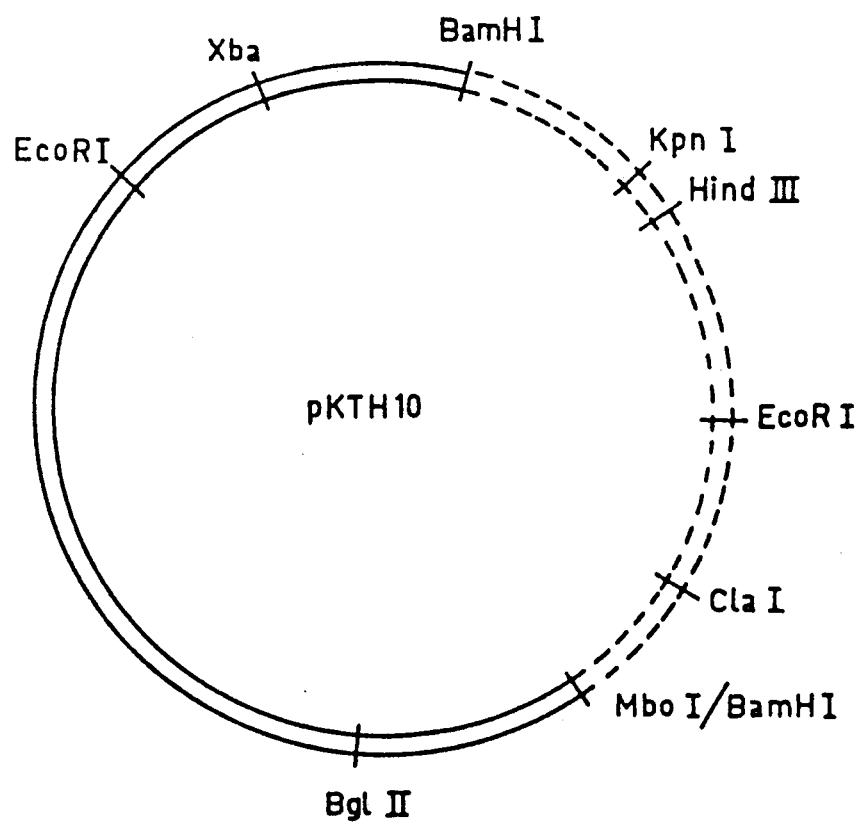
FIG. 2 depicts the pkTH10 of the resulting recombinant DNA molecule, the exclusive restriction enzyme cleavage sites in the α-amylase gene or its regulation part, and the general structure of the recombinant DNA molecule.

The recombinant DNA molecule is isolated from the *B. subtilis* strain and characterized by restriction enzymes and definition of the nucleotide sequence. FIG. 2 shows the pKTH10 of the obtained recombinant DNA molecule, the exclusive restriction enzyme cleavage sites in the α-amylase gene or its regulation part, and the general structure of the recombinant DNA molecule. FIG. 3 shows part of the α-amylase gene base order starting at the cleavage site of the restriction enzyme EcoR I.

The recombinant DNA molecule concerned in this invention consists of the regulation and excretion signals of the *Bacillus* strain α-amylase gene, and of a plasmid molecule that is present in the *Bacillus* strain bacteria in several copies in such a manner that the gene of any protein can be joined at the end of the excretion signal of the α-amylase gene, whereby the desired protein can be produced in the *Bacillus* strain bacterium.

Most of the α-amylase structure gene is first removed by EcoR I restriction enzyme treatment from the recombinant DNA molecule containing the α-amylase gene. The obtained DNA molecule is cleaved by the restriction enzyme and shortened by exonuclease III and S1 nuclease or by exonuclease BAL 31 to remove the remaining structure part of the α-amylase gene, whereafter it is ensured by a reverse transcriptase enzyme that the ends of the molecule are double-stranded. A DNA linker molecule is then joined to the cleaved and shortened molecule. The location of the DNA linker molecule in the recombinant DNA molecule is determined by defining the DNA nucleotide sequence at the joining site. At this restriction enzyme cleavage site of the DNA linker molecule it is possible to join the structure gene of any other protein, for example, the β-lactamase of *E. coli*, or the DNA sequence or part of it of any α-, β- or γ-interferon coding for amino acids. The protein coded by the joined gene will then be produced in the *Bacillus* strain bacterium by the aid of the regulation and excretion signals of the α-amylase gene.

By the new method it is possible to produce any of the following proteins:

A. Antigenic proteins of microbes and protozoa

Capsule, outer membrane and Fimbria proteins from the following sources:

*Bacteroides fragilis*
*Fusobacterium spp.*
*Bordetella pertussis*
*Haemophilus influenzae*
*Versinia enterocolitica*
*Yersinia pestis*
*Branhamella catarrhalis*
*Escherichia coli*
*Klebsiella pneumonia*
*Vibrio cholerae*
*Proteus mirabilis*
*Pseudomonas aeruginosa*
*Serratia marcescens*
*Legionella pneumophila*
*Neisseria gonorrhoeae*
*Neisseria meningitidis*
*Salmonella typhimurium*
*Salmonella typhi*
*Salmonella paratyphi* B
*Mycobacterium tuberculosis*
*Chlamydia trachomatis*
*Shigella spp.*

Protein toxins produced by the following bacteria:
*Staphylococcus aureus*
*Pseudomonas aeruginosa*
*Clostridium spp.*
*Escherichia coli*

Yersinia pestis
Vibrio cholerae
Bordetella pertussis
M-Protein of the *Streptococcus pyogenes* bacterium
Excreted enzymes of *Streptococcus mutans*

Surface proteins of the following organisms:

*Plasmodium spp.*
*Toxoplasma spp.*
*Leishmania sp.* } all phases of development
*Schistosoma spp.*
*Trypanosoma spp.*

Membrane proteins of the following microorganisms:

*Mycoplasma pneumoniae*
*Mycoplasma hominis*
Contaqious protein of *Streptococcus spp.*
Contaqious protein of *Staphylococcus aureus*

B. Antigen proteins of viruses

HA and NA proteins of myxoviruses (influenza A H1, H12, influenza B, influenza C)

HN and F proteins of paramyxoviruses (parainfluenza 1-4, Newcastle disease virus, Measles virus, Respiratory syncytial virus, Parotitis virus, Distemper virus)

G protein of Rabies virus

E1 and E2 proteins of alfaviruses (Chikungunya, Western, Eastern, Venzuelan equine encephalitis virus, O'nyong-nyong virus, Semliki Forest virus, Sindbis virus)

V1 and V3 proteins of flavin viruses (Denque 1-4, Japanese encephalitis virus, Mite encephalitis viruses, Murray Valley encephalitis virus, Kyasanur Forest disease virus, Looping ill virus, Omsk hemorrhagic fever virus)

Surface proteins of German measles virus

Surface proteins of Hog Cholera virus

Surface proteins of Equine arthritis virus

G1 and G2 proteins of Bunya viruses (Rift Valley fever virus, Crimean hemorrhagic fever virus, California encephalitis virus, Phlebotomus fever virus)

G1 and G2 proteins of arena viruses (Lassa fever virus, Lymphocytic chorion meningitis virus)

Proteins V1-V4 of picorna viruses (polio 1-3, Coxsackie A viruses 1-24, Coxsackie B viruses 1-6, ECHO viruses 1-8, 11-34, Hepatitis A virus, Human rhino viruses 1-113)

Surface proteins of rota viruses

Surface proteins of herpes viruses (HSV 1, 2, Cytomegalo virus, Epstein-Barr virus, Equine abortion virus)

VP1-VP3 proteins of papova viruses (BK virus, Human wart virus)

Proteins of parvo viruses (Mink enteritis virus, Bovine parvo virus, Feline parvo virus, Procine parvo virus)

Structure proteins of Human hepatitis B virus

Surface proteins of Ebola and Marburg viruses

Hexone, pentone and fiber proteins of adeno viruses (Human adeno viruses 1-33).

C. Industrial enzymes

| Enzymes: | |
|---|---|
| α-amylase | (*B. subtilis*, malt, *A. oryzae*) |
| Amino acid acylase | (*Bacillus spp.*) |
| Amyloglucosidase | (*A. niger*, *Rhizopus sp.*) |
| Bromelain | (Ananas) |
| Phisine | (Fig) |
| β-galactosidase | (*A. niger*) |
| β-glucanase | (*B. subtilis*, *Aspergillus sp.*) |
| Glucose isomerase | (*L. brevis*, *P. notanum*, *Streptomyces sp.*) |

-continued

| Enzymes: | |
|---|---|
| Glucose oxidase | (*A. niger*) |
| Hemicellulase | (*A. niger*, *Trichoderma reesei*, *Bacillus spp.*) |
| Invertase | (*S. cerevisiae*) |
| Catalase | (*A. niger*) |
| Collagenase | (*Clostridium histolyticum*) |
| Xsylanase | (*A. niger*, *Trichoderma reesei*, *Bacillus spp.*) |
| Lactase | (*S. fragilis*, *S. lactis*, *E. coli*, *Aspergillus sp.*) |
| Lipase | (Mould, Yeast) |
| Naringinase | (*A. niger*) |
| Pancreatin | (Pancreas) |
| Papain | (Papaya) |
| Pectinase | (*A. niger*, *Penicillium sp.*) |
| Penicillinamidase | (*Bacillus spp.*) |
| Penicillinase | (*Bacillus spp.*) |
| Pepsin | (Animal abdomen) |
| Protease | (*A. oryzae*, *B. subtilis*) |
| Pullulanase | (*Aerobacter aerogenes*) |
| Isoamylase | (*Escherichia intermedia*, *Pseudomonas sp.*) |
| Rennin | (Calf stomach, *M. miehei*, *Endothia parasitica*) |
| Ribonuclease | (*B. subtilis*, Yeast, *A. niger*) |
| Cellulase | (*A. niger*, *Trichoderma reesei*) |
| Streptokinase | (*Streptococcus hemolyticus*) |
| Trypsin | (Pancreas) |

DETAILED DESCRIPTION OF THE PREPARATION OF RECOMBINANT DNA MOLECULES AND THEIR TRANSFER INTO THE HOST BACTERIUM, AND OF THE PRODUCTION OF SELECTED PROTEINS

Isolation, purification and cleavage of the genome from *Bacillus* strain bacteria

*B. amyloliquefaciens* strain was used as the bacterium strain. The strain was grown over night in a rich nutrient solution, the cells were harvested and washed in a 0.0015M sodiumcitrate—0.015 NaCl buffer. The washed cells were suspended ($2\times10^{11}$ cells, i.e. a culture of 200 ml) in 2 ml of 20% w/v sucrose—50 mM Tris-HCl solution (pH 8.0). 20 mg lysozyme, 20 mg pronase and 2 ml 1% w/v Sarkosyl $^R$—0.1M EDTA solution (pH 8.0) were added, and the solution was incubated for 15 hours at 37° C. 6.5 ml $H_2O$ and such an amount of solid CsCl as to make the refraction index of the lysate 1.4100, were added to the obtained lysate, whereafter the lysate was centrifuged (Beckman Ti 50 rotor, 36,000 rpm, 48 hours, 10° C.). The centrifuged lysate was divided into fractions, and those fractions that were presumed to contain the bacterial genome on the basis of the viscosity were collected and dialysed for 30 hours against a 10 mM Tris-HCl—1 mM EDTA—0.1M NaCl buffer (pH 8.0) at 4° C.

The obtained genome preparation was extracted three times with phenol, and the phenol was removed by ether extraction. The DNA was purified by centrifugation in linear 15→30% w/v sucrose—0.1M NaCl—50 mM Tris-HCl—1 mM EDTA, 0.1% sodium lauryl sulphate (pH 8.0) gradient (Beckman SW27 rotor, 22,000 rpm, 16 hours, 22° C.), whereafter the gradient was fractioned, and those fractions were collected whose DNA sequences were $\geqq 15\times10^6$ dalton, and the DNA was precipitated by ethanol.

The genome preparation of *B. amyloliquefaciens* thus isolated was incompletely cleaved by the restriction enzyme Mbo I, and the cleaved DNA sequences were sorted out according to their size in the above sucrose gradient (Beckman SW27 rotor, 22,000 rpm, 16 hours, 22° C.). Those fractions whose DNA sequences were $1.5-5 \times 10^6$ dalton were recovered and the DNA was precipitated by ethanol.

Isolation and cleavage of the transfer vector by restriction enzyme

The plasmid pUB 110 was used as a transfer vector. The plasmid was isolated and purified from the *Bacillus subtilis* strain SB202 as described earlier (Gryczan et al., J. Bacteriol. 134: 318-329, 1978). The purified plasmid preparation was cleaved with the restriction enzyme BamH I, which has only one cleavage site in the plasmid molecule. The linearity of the plasmid molecule was controlled by gel electrophoresis.

Combination of the *B. amyloliquefaciens* genome strands to the transfer vector The *B. amyloliquefaciens* genome strands that had been cleaved by the enzyme Mbo I and selected on the basis of the size were mixed with the pUB 110 plasmid cleaved by the enzyme BamH I in 10 mM Tris-HCl−1 mM EDTA buffer (pH 8.0) in a DNA molar ratio of 1:3, with the total volume of 120 μl and with the total DNA concentration of 180 μg/ml. The mixture was heated for 5 minutes at 65° C., and 13 μl 66 mM Tris-HCl−6.6 mM $MgCl_2$−10 mM dithiothreitol−1 mM ATP buffer (pH 7.8) and 5 μl $T_4$-DNA ligase (20 Weiss units) were added to the chilled solution. The ligase mixture was incubated for 3 hours at 23° C., and the ligation result was controlled by gel electrophoresis.

Transfer of the recombinant DNA molecule into the host bacterium

A *Bacillus subtilis* 1A197 strain with the genotype sacA321, metB5, aro I 907, amy$^-$ was used as the host bacterium. The strain was obtained from Bacillus Genetic Stock Center (Ohio State University, U.S.A.), and its phenotype Amy$^-$ was mapped by bacteriogenetic methods as mutations in the structure gene of the enzyme coding for α-amylase. The strain was made competent, i.e. capable of receiving DNA in a manner described previously (Anagnostopoulos et al., J. Bacteriol. 81: 741-746, 1961). The recombinant DNA molecules prepared by ligation in the above section were mixed with the competent host bacteria, and the mixture was kept 30 minutes at 37° C. The mixture was then spread on bacterium plates in which kanamycin antibiotics was used to prevent the growth of all those bacteria that had not received a plasmid. The plates were kept for 30 hours at 37° C., during which time the host bacteria that had received a plasmid or a *B. amyloliquefaciens* genome strand joined to it grew into small colonies.

Detection of host bacteria in which the *B. amyloliquefaciens* gene coding for α-amylase is joined to plasmid pUB 110

The bacterial colonies described above were replicated on new nutrient plates that were grown for 30 hours at 37° C. The obtained bacterial cultures were treated with I-KI solution according to a method described earlier (J. Bacteriol. 119: 416-424, 1974), which resulted in a white ring forming round those bacterial colonies that had received a recombinant DNA molecule containing a gene coding for α-amylase. The corresponding colony of such a colony was collected from the original bacterium plate and the bacteria therein were subjected to several successive purification growths.

Isolation and characterization of the recombinant DNA molecule

The recombinant DNA molecule was isolated and purified from the host bacterium by a method described earlier (Gryczan et al., J. Bacteriol. 134: 318-329, 1978). The molecule was characterized by means of various restriction enzymes, and the location of the gene coding for α-amylase was preliminary determined by following the inactivation of the gene when joining extra DNA sequences at various sites of the recombinant DNA molecule. The nucleotide sequence of the gene coding for α-amylase was then determined by a method described earlier (Maxam, A. and Gilbert, W., Proc. Natl. Acad. Sci. U.S.A. 74: 560-564, 1977).

Removal of the EcoR I fragment from the plasmid pKTH10

The plasmid pKTH10 was cleaved at the cleavage site EcoR I (FIG. 2). The obtained DNA sequences (about 1 μg) were ligated together again in 66 mM Tris-HCl−6.6 mM $MgCl_2$−10 mM dithiothreitol−10 mM ATP buffer (pH 7.8) to which 0.5 μl $T_4$-DNA ligase (2 Weiss units) was added. The ligation mixture was incubated for 3 hours at 23° C., whereafter the competent *B. subtilis* IHO 6064 strain was transformed by it in the manner described above. The cells were spread on bacterium plates containing kanamycin and grown over night at 37° C. An α-amylase-negative colony was screened from the obtained transformants by I-KI method using starch plates and a plasmid was isolated from this in a manner described earlier (Gryczan et al., J. Bacteriol. 134: 318-329, 1978). The missing EcoR I - Kpn I - Hind III - EcoR I fragment in the obtained plasmid preparation pKTH29 was controlled by gel electrophoresis.

Shortening of the plasmid pKTH29 by exonuclease treatment

The plasmid pKTH20 (100 μl, 500 μg/ml) was cleaved by the restriction enzyme EcoR I. After this treatment, 0,5 μl 1M dithiothreitol and 10 μl exonuclease III (0.25 units, Biolabs) were added to the solution. The solution was incubated for 1-3 minutes at 37° C., and the reaction was stopped in a 70° C. waterbath. The DNA was precipitated from the solution by ethanol and dissolved in a 0.3M NaCl−0.03M sodium acetate−3 mM $ZnCl_2$ buffer (pH 4.5). 10 μl S1-nuclease (25 units/ml, Boehringer Mannheim) was added to this and the solution was incubated for 30 minutes at 37° C. and for 10 minuted at 4° C. After the incubations, the preparate was extracted with phenol, the phenol was removed by ether extraction, and the DNA was precipitated by ethanol. The dried DNA was dissolved in 40 μl 10 mM Tris-HCl−1 mM EDTA buffer (pH 8.0), and 10 μl 150 mM Tris−180 mM KCl−40 mM $MgCl_2$−3.0 mM dithiothreitol buffer (pH 8.3), 5 μl dNTP mixture, in which to each nucleotide triphosphate 10 mM of the solution was mixed in equimolar ratio, and 2 μl reverse transcriptase enzyme (Beard, 13 units/μl), were added. The solution was incubated for 30 minutes at 37° C. and the reaction was stopped by incubation at 65° C. for 7 minutes. The DNA was purified by preparative agarose electrophoresis (LGT, Low Gelling Temperature), and the plasmid zones that had been stained with ethidium bromide were cut off from the gel. The DNA was extracted from the agarose by phenol at 65° C., the phenol extraction was repeated at 20° C., and the phenol was removed by ether extraction. The DNA was precipitated by ethanol, the precipitate was washed with 70% ethanol and dried.

Phosphorylation of the linker molecule and its combination to the plasmid

5 μl $^{32}$PγATP (10 mCi/ml, 3000 Ci/mmol), 1.74 μl 600 mM Tris-HCl—66 mM $MgCl_2$—100 mM dithiothreitol buffer (pH 8.0) and 0.5 μl $T_4$-polynucleotidekinase were added to 10 μl EcoR I linker molecule solution (EcoR I linker, Collaborative Research, 50 μg/ml). The solution was incubated for 30 minutes at 37° C., whereafter 5 μl 10 mM ATP was added, and the incubation was continued for 30 minutes at 37° C. The above described dried pKTH29 preparate that had been treated with exonuclease was dissolved in 5 μl of the above described solution containing phosphorylated EcoR I linker molecule. 0.5 μl 10 mM ATP, 0.5 μl 1 mM spermidine and 0.5 μl $T_4$-DNA-ligase (2 Weiss units) were added to the solution. The solution was incubated for 3 hours at 23° C., whereafter it was diluted to 20 μl 40 mM Tris-HCl-100 mM NaCl-10 mM $MgCl_2$-buffer (pH 7.6). 15 units of EcoR I enzyme (Biolabs) were added to this, and the solution was incubated for 12 hours at 37° C. The reaction was stopped by incubation at 65° C. for 10 minutes. The preparate treated with EcoR I was gelfiltered through 1 ml Sepharose 4B column. 2 mM Tris-HCl-0.1 mM EDTA buffer (pH 7.5) was used as eluation buffer in the filtering. The filtrate was harvested in 35 μl fractions, and the fractions containing plasmid were identified by their radioactivity, collected and dried. The dried DNA was dissolved in 20 μl 66 mM Tris-HCl-6.6 mM $MgCl_2$-10 mM dithiothreitol buffer (pH 8.0), and 1.5 μl 10 mM ATP and 0.3 μl $T_4$-DNA-ligase were added to this. The solution was incubated for 3 hours at 23° C., whereafter the competent *B. subtilis* IHO 6064 strain was transformed by the plasmid preparation, and the cells were cultivated on bacterium plates containing kanamycin.

The plasmids were isolated from the transformants by a method described earlier (Gryczan et al., J. Bacteriol. 134: 318–329, 1978), and the plasmids were first characterized by gel electrophoresis, whereafter their DNA nucleotide sequence on both sides of the EcoR I linker molecule was determined. In this way, the plasmid pKTH 38 was obtained from the plasmid pKTH 29. In the plasmid pKTH 38, the EcoR I linker molecule is located 90 nucleotide pairs after the cleavage site of the excretion signal in the area of the α-amylase structure gene. In order to join the linker molecule at the joining site of the excretion signal or in the immediate vicinity thereof, the plasmid pKTH 38 was cleaved with EcoR I. Three portions of 10 μg of the cleaved plasmid were each suspended in 115 μl 20 mM Tris, 600 mM NaCl, 12 mM $MgCl_2$, 12 mM $CaCl_2$, 1 mM EDTA buffer (pH 8.1). 10 μl BAL-31 enzyme (Bethesda Research Laboratories, BRL, 40 U/ml) was added to each plasmid portion, and the tubes were incubated for 5, 6 and 7 minutes in a water bath of 30° C. The reaction was stopped by adding 0.5M EDTA, pH 8.0, so as to obtain a final concentration of 12 mM. The DNA portions treated with BAL-31 were combined, extracted twice with phenol and precipitated with ethanol. The ethanol precipitate was suspended in 75 μl 63 mM Tris, 6.3 mM $MgCl_2$ buffer (pH 8.0), and to the solution were added 5 μl 1 mM dATP, 1 mM dGTP, 1 mM dCTP, and 1 mM dTTP, and finally 5 μl $T_4$-polymerase (PL-Biochemicals, 5 U/μl). The solution was incubated for 80 minutes at 11° C. The reaction was stopped by adding 0.5 EDTA as above, and the solution was extracted with phenol and the DNA was precipitated with ethanol. The ethanol precipitate was dissolved in 250 μl 10 mM Tris, 1 mM EDTA buffer (pH 8.0). To 55 μl of this solution were added 50 μl phosphorylated Hind III linker molecule (BRL, 75 pmol), 5 μl 660 mM Tris, 100 mM $MgCl_2$, 50 mM dithiothreitol buffer (pH 7.5), and 10 μl $T_4$-DNA-ligase (BRL, 2 U/μl). The mixture was incubated for 15 hours at 15° C. and for 10 minutes at 65° C. The DNA was precipitated by adding isopropanol, the DNA precipitate was washed with 70% ethanol and, after drying in vacuo, suspended in 100 μl 10 mM Tris, 50 mM NaCl, 5 mM MgCl, 5 mM dithiothreitol buffer (pH 8.0). 3 μl of Hind III restriction enzyme (BRL, 10 U/μl) was added to the suspension, and the solution was incubated for 4 hours at 37° C. and for 10 minutes at 65° C., the DNA was purified by electrophoresis, 0.8% LGT agarose gel (Marine Colloids Inc.), 30 V, 15 hours. The linear plasmid zone was cut off from the gel, the DNA was extracted at 65° C. with phenol and was precipitated with ethanol. The ethanol precipitate was dissolved in 35 μl 66 mM Tris, 10 mM MgCl, 5 mM dithiothreitol buffer (pH 7.5) to which was added 1.5 μl 10 mM rATP and 1.5 μl $T_4$-DNA-ligase (BRL, 2 U/μl). The mixture was incubated for 3 hours at 22° C. and transformed into the competent *B. subtilis* IHO 6135 strain, and the cells were cultivated on nutrient medium plates containing kanamycin. The plasmids were isolated from the transformants according to a method described earlier, and the location of the Hind III linker molecule in the plasmids was determined by means of DNA sequencing. In this way a series of plasmids was obtained in which the Hind III linker molecule is located immediately after the excretion signal or in different positions after the cleavage site of the excretion signal in the area of the α-amylase structure gene:

```
              -31                    -3   -1   +1
              Met Phe Gln        Thr Ser  Ala  Val Asn Gly Thr Leu Met Gln Tyr Phe Glu Trp Tyr Thr Pro Asn
              ATG ATT CAA ...    ACA TCA  GCC| GTA AAT GGC ACG CTG ATG CAG TAT TTT GAA TGG TAT ACG CCG AAC
pKTH 10
pKTH 50       ATG ATT CAA ...    ACA TCA  GCC| [GCAAGCTTGC]
pKTH 51       ATG ATT CAA ...    ACA TCA  GCC| [GCAAGCTTGC]
pKTH 52       ATG ATT CAA ...    ACA TCA  GCC| G [GCAAGCTTGC]
pKTH 53       ATG ATT CAA ...    ACA TCA  GCC| GTA AAT GGC AC [GCAAGCTTGC]
pKTH 54       ATG ATT CAA ...    ACA TCA  GCC| GTA AAT GGC ACG [GCAAGCTTGC]
pKTH 55       ATG ATT CAA ...    ACA TCA  GCC| GTA AAT GGC ACG C [GCAAGCTTGC]
pKTH 56       ATG ATT CAA ...    ACA TCA  GCC| GTA AAT GGC ACG CT [GCAAGCTTGC]
pKTH 57       ATG ATT CAA ...    ACA TCA  GCC| GTA AAT GGC ACG CTG ATG CAG TAT TTT G [GCAAGCTTGC]
pKTH 58       ATG ATT CAA ...    ACA TCA  GCC| GTA AAT GGC ACG CTG ATG CAG TAT TTT GAA TGG [GCAAGCTTGC]
pKTH 59       ATG ATT CAA ...    ACA TCA  GCC| GTA AAT GGC ACG CTG ATG CAG TAT TTT GAA TGG TAT ACG CCG [GCA....]
```

The DNA sequence coding for the amino acids of any desired protein can be joined to the cleavage sites formed by these Hind III linker molecules whereby, as appears from the above examples, a bacterium of the Bacillus strain will produce and excrete said protein on this substrate.

EXAMPLE 1

Production of the β-lactamase enzyme of E. coli in the Bacillus subtilis strain

The plasmid pKTH was opened by the Hind III enzyme, and to the cleavage site was joined a gene coding for β-lactamase of E. coli from which the promotor and excretion signal areas had been removed. The hybrid plasmid obtained was transformed into the competent B. subtilis strain by selecting the cells that had received the plasmid, on the basis of the kanamycin resistance, and the cells were cultivated on nutrient medium plates containing kanamycin. The transformants were screened with respect to the yield of β-lactamase by suspending each colony in 100 μl 0.1 mM nitrosephin, 0.1M K-phosphate solution (pH 7.0). Liquid cultures were made of the colonies which gave a positive result in the nitrosephin test (the colour of the solution changed into red) for determination of the activity of the β-lactamase enzyme produce. The IHO 6140-B. subtilis strain which had been transformed by the plasmid pKTH 50 was used as control. The strains were grown in a SMS solution (Spizizen minimal salts) to which had been added 0.5% glycerol, 1% soluble starch, and 5 μg/ml kanamycin. The cultures were grown at 37° C. while shaking. About 5 hours after a logarithmic growth period (Klett$_{67}$~250), the cultures were centrifuged 10.000 g 5 minutes and the supernatant was recovered. The cells were suspended in 0.1M potassium phosphate buffer (pH 7.0) to their original growing volume. The β-lactamase activity was determined in the cell and supernatant fractions by following spectrophotometrically the disintegration of nitrosephin. The following results were obtained from the determination.

|  | β-lactamase activity (U/ml)* | |
|---|---|---|
|  | cells | supernatant |
| B. subtilis IHO 6140/pKTH 50 β-lactamase | 60 | 3 000 |
| B. subtilis IHO 6140/pKTH 50 | <10 | <10 |

*1U of β-lactamase disintegrates 1 μmol penicillin G in 1 minute at 37° C.

EXAMPLE 2

Production of leucocyte interferon in the Bacillus subtilis strain

The plasmid pKTH 53 was cleaved by the Hind III enzyme, and to the cleavage site was joined the DNA sequence coding for the leucocyte interferon (α-2) from which the part coding for the excretion signal had been removed. The obtained hybrid plasmid was transformed into the competent IHO 6140 B. subtilis strain by selecting the cells that had obtained the plasmid, on the basis of the kanamycin resistance. The transformants were screened by a colony hybridization method (Grünstein, M. and Hogness, D. S., Proc. Natl. Acad. Sci. (U.S.) 72: 3961–3965, 1975) while using as probe the DNA coding for the interferon, maked $^{125}$I. The bacterium colonies containing interferon-DNA were grown in Luria broth to which had been added 2% soluble starch and 5 μg/ml kanamycin, while shaking at 37° C. The culture was centrifuged 4 hours after the logarithmic growth period (Klett$_{67}$~300) 10.000 g, 5 minutes. The supernatant was recovered, and the cells were suspended to their original growing volume in a 0.9% NaCl solution. The interferon activity was determined in the cell and supernatant fractions. The B. subtilis IHO 6140/pKTH 53 strain was used as control in the determinations. The following results were obtained from the determinations:

|  | Interferon activity (I.U.(ml)) | |
|---|---|---|
|  | cells | supernatant |
| B. subtilis IHO 6140/pKTH 53-IF | 3 000 | 200 000 |
| B. subtilis IHO 6140/pKTH 53 | <20 | <20 |

EXAMPLE 3

Production of Semliki Forest virus E1-protein in the Bacillus subtilis strain

Figure 4:
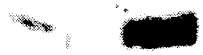
FIG. 4 is the immunoelectrophoresis pattern of the expression and excretion of E1-protein in *B. subtilis* IHO 6140 strain.

The plasmid pKTH 51 was cleaved by the Hind III enzyme, and to the cleavage site was joined the gene (complementary DNA prepared from SFV genome by reversetranscriptase) coding for the Semliki Forest virus E1-protein from which the promotor, excretion signal and the DNA sequence coding for the hydrophobic end part of the E1-protein had been removed. The obtained hybrid plasmid was transformed into the competent B. subtilis IHO 6140 strain by selecting the cells that had obtained the plasmid, on the basis of the kanamycin resistance. The transformants were screened with respect to the DNA sequence coding for E1-protein using the colony hybridization method (Grünstein, M. and Hogness, D. S., Proc. Natl. Acad. Sci. (U.S.) 72; 3961-3965, 1975). From the positive colonies the right direction of the E1-insert was ensured by restriction enzyme survey. The bacterium colonies were grown in Luria broth to which had been added 10 μg/ml kanamycin, and of the end of the growing period 1 mM phenylmethylsulphonylfluoride. The amount of E1-protein formed was determined in the cell and supernatant fractions by immunoelectrophorese technique. The results are shown in FIG. 4; more than 90% of the synthetized E1-protein is excreted into the culture medium.

What I claim is:

1. A method for the preparation of a selected protein or polypeptide in Bacillus strain bacteria by joining DNA coding for the selected protein or polypeptide to a bacterium gene, comprising the successive steps of:
   (1) cleaving the Bacillus amyloliquefaciens gene for α-amylase at a location to the 3' side of the excretion signal downstream from the regulation signal of the α-amylase gene or at a location downstream from a portion of the DNA sequence essential with respect to excretion of the α-amylase protein;
   (2) joining the cleaved gene to a plasmid present in Bacillus strain bacteria;
   (3) joining the DNA sequence coding for the selected protein or polypeptide to the cleavage site;
   (4) transforming the Bacillus strain host bacteria with the recombinant DNA molecules so obtained; and
   (5) cultivating the transformed host bacteria for producing the selected protein or polypeptide.

2. A method as claimed in claim 1 in which the DNA sequence coding for the amino acids in the selected protein or polypeptide is joined to a nucleotide sequence selected from the group consisting of:

5' CTG TTA TTT GTC AGT TTG CCG ATT ACA AAA ACA TCA GCC,

5' CTG TTA TTT GTC AGT TTG CCG ATT ACA AAA ACA TCA GCC G,

5' CTG TTA TTT GTC AGT TTG CCG ATT ACA AAA ACA TCA GCC GT,

5' CTG TTA TTT GTC AGT TTG CCG ATT ACA AAA ACA TCA GCC GTA,

5' CTG TTA TTT GTC AGT TTG CCG ATT ACA AAA ACA TCA GCC GTA A, and,

5' CTG TTA TTT GTC AGT TTG CCG ATT ACA AAA ACA TCA GCC GTA AA.

3. A method as claimed in claim 1 in which the selected protein or polypeptide is any of the α- or β-interferons.

4. A method as claimed in claim 1 in which the selected protein or polypeptide is *E. coli* β-lactamase.

5. A method as claimed in claim 1 in which the host bacterium is *B. subtilis*.

6. A method for the preparation of a selected protein or polypeptide in a *Bacillus subtilis* host, comprising the steps of joining DNA coding for the selected protein or polypeptide to a recombinant plasmid vector obtained by cleaving a gene encoding a Bacillus strain protein or polypeptide at a location to the 3' side of the excretion signal downstream from the regulation signal, or at a location downstream from a portion of the DNA sequence essential with respect to the excretion of said Bacillus strain protein or polypeptide, joining the cleaved gene to a plasmid present in Bacillus strain bacteria, transforming the *Bacillus subtilis* host with the recombinant DNA molecules so obtained, and cultivating the transformed host to produce excretable protein or polypeptide, wherein the DNA sequence coding for the selected protein or polypeptide is joined to a recombinant plasmid vector comprising a plasmid present in Bacillus strain bacteria, and the regulation signal of the gene coding for *Bacillus amyloliquefaciens* α-amylase and the excretion signal or a part thereof essential with respect to the excretion of said α-amylase.

7. A method as claimed in claim 6 in which the DNA sequence coding for the selected protein or polypeptide is a gene coding for any of the α- or β-interferons.

8. A method as claimed in claim 6 in which the DNA sequence coding for the selected protein or polypeptide is a gene coding for *E. coli* β-lactamase.

* * * * *